United States Patent
Nakamura et al.

(10) Patent No.: US 10,954,336 B2
(45) Date of Patent: Mar. 23, 2021

(54) CYCLIC POLY L-LACTIC ACID

(71) Applicant: SCRUM Co., Ltd., Chiba (JP)

(72) Inventors: Hitoshi Nakamura, Chiba (JP); Susumu Sugiki, Chiba (JP)

(73) Assignee: SCRUM CO., LTD., Chiba (JP)

( * ) Notice: Subject to any disclaimer, the term of this patent is extended or adjusted under 35 U.S.C. 154(b) by 0 days.

(21) Appl. No.: 16/495,163

(22) PCT Filed: Aug. 29, 2018

(86) PCT No.: PCT/JP2018/032790
§ 371 (c)(1),
(2) Date: Sep. 18, 2019

(87) PCT Pub. No.: WO2019/082516
PCT Pub. Date: May 2, 2019

(65) Prior Publication Data
US 2020/0087449 A1 Mar. 19, 2020

(30) Foreign Application Priority Data
Oct. 24, 2017 (JP) .............................. JP2017-216782

(51) Int. Cl.
*C08G 63/08* (2006.01)
*A61K 31/765* (2006.01)
*C07D 319/12* (2006.01)

(52) U.S. Cl.
CPC ............ *C08G 63/08* (2013.01); *A61K 31/765* (2013.01); *C07D 319/12* (2013.01)

(58) Field of Classification Search
USPC .................................................. 528/271, 272
See application file for complete search history.

(56) References Cited

U.S. PATENT DOCUMENTS

2004/0258657 A1* 12/2004 Watanabe ............... A61P 35/00
424/78.37

FOREIGN PATENT DOCUMENTS

| JP | 2000-239171 | 9/2000 |
|---|---|---|
| JP | 2001-139476 | 5/2001 |
| JP | 2004-155670 | 6/2004 |
| JP | 2006-232909 | 9/2006 |
| JP | 2007-112751 | 5/2007 |
| JP | 2013-39117 | 2/2013 |
| JP | 5966230 | 8/2016 |
| JP | 6331182 | 5/2018 |

OTHER PUBLICATIONS

International Search Report dated Nov. 20, 2018 in International Application No. PCT/JP2018/032790.

* cited by examiner

*Primary Examiner* — Terressa Boykin
(74) *Attorney, Agent, or Firm* — Wenderoth, Lind & Ponack, L.L.P.

(57) ABSTRACT

A cyclic poly L-lactic acid composition having a pH of 6 to 7 by the polymer itself.

4 Claims, 6 Drawing Sheets

Mass spectrum (MALDI)

Mass spectrum (MALDI, enlarged)

Mass spectrum (ESI+)

Mass spectrum (ESI+, enlarged)

CYCLIC POLY L-LACTIC ACID

TECHNICAL FIELD

The present invention relates to a cyclic poly L-lactic acid (composition) having a specific pH by the polymer itself (alone), a method for producing the same, a pharmaceutical product containing the cyclic poly L-lactic acid (composition), and the like.

TECHNICAL BACKGROUND

L-lactic acid is one of the products of glycolysis in vivo. When rapid exercise is performed, sugar is decomposed as an energy source in muscle cells to produce lactic acid via pyruvic acid. Microorganisms that synthesize L-lactic acid by decomposing carbohydrates (lactic acid fermentation) are collectively called lactic acid bacteria. Lactic acid is contained in various processed foods such as yogurt, cheese, butter, pickles, and sake, and is applied in food industries. Lactic acid is used as a food additive to acidify the food, as pH-adjusting agent, and as antiseptic agent to prevent the propagation of germs in the foods.

L-lactic acid is obtained by the fermentation with the lactic acid bacteria of saccharides such as starch and sugar obtained from natural raw materials such as potato, corn, sugar beet, sugar cane, etc. It is thus derived from plants, and has a molecular formula of C3H6O3, a molecular weight of 90.08, pH 1 or less. Its L-type exists as a colorless solid having a melting point of 53° C., and as a viscous liquid at room temperature. All types are highly hygroscopic, well dissolved in water, alcohol, and ether, and its aqueous solution shows acidity.

Lactide and Dilactide are ester condensation of 2 molecules of lactic acid, and a cyclic compound having a molecular formula of C6H8O4 and a molecular weight of 144.13. Lactide is synthesized by heating lactic acid, and the lactide of lactic acids undergoes ring-opening polymerization to become poly lactic acid. The poly lactic acid is hydrolyzed by water in the environment to be depolymerized, and finally decomposed into carbon dioxide and water by microorganisms and the like. The lactide is a raw material of the poly lactic acid for industrial products.

The poly lactic acid is classified into polyesters having a molecular weight of 90.000 to 280.000, which is a long-chain polymer polymerized by ester bonds. As the poly lactic acid having a high molecular weight is biodegradable and bioabsorbable substance, it is decomposed into compounds by hydrolysis of the ester bonds in vivo. It is therefore used as a material for biomedical instruments, surgical sutures and absorbable implant products.

The poly lactic acid having the high molecular weight is also a biodegradable plastic. The biodegradable plastic is a plastic that is easily degraded by microorganisms, which is used in films, sheets, textiles, food containers, and OA equipment.

Cyclic poly L-lactic acid (Cyclic polymerized L-lactic acid) is a polymerized material with a structure in which the L-lactic acid is linked in a cyclic manner. The L-lactic acid with a cyclic structure is a polymer having the same biological activity as that originally produced by human cells. It is a kind of a regulatory substance secreted from the cell, which is taken into the body and involved in the improvement of cell functions. It is a biodegradable and bioabsorbable substance, and is involved in the generation of intracellular energy in the body. The cyclic poly L-lactic acid has a low molecular weight of 2,000 or less, and is used in pharmaceuticals, foods, drinking water, and health foods.

FIG. 1 shows a mass spectrum of poly-L-lactic acid obtained in Production Example 1 of Patent Document 1. (Unit: m/z 72) Ionic strength: M/Z 145 for n=2, M/Z 217 for n=3. According to the production method by dehydration polymerization with simple heating, heating in an atmosphere of an inert gas such as nitrogen gas under a normal or reduced pressure, ionic strength of 60% to 70% or less for the degree of polymerization of L-lactic acid molecules of n=2 to n=3. The properties of the L-lactic acid monomer strongly remain in the degree of polymerization of L-lactic acid n=2 (lactide) and n=3, and their molecular weight is small. Accordingly, the energy generated by their ring-opening polymerization will be small. Furthermore, M/Z 289 for n=4 has an ionic strength of about 30%, and M/Z 361 for n=5 to M/Z 833 for n=12 have an ionic strength of 15% or less, M/Z 977 for n=14 to M/Z 1337 for n=19 have an ionic strength of 10% or less. Thus, the substances of the degree of polymerization of from M/Z 617 for n=9 to M/Z 1337 for n=19 do not have enough ionic strength.

Claim 1 of Patent Document 2 discloses that L (+) lactic acid was subjected to dehydration condensation in a nitrogen gas atmosphere by stepwise pressure reduction and temperature elevation, and ethanol and methanol soluble components of the resulting reaction solution were dried under reduced pressure. They were subjected to a reversed phase ODS column chromatography and eluted with 25 to 50% acetonitrile aqueous solution at pH 2.0, followed by the separation and purification of a mixed poly L-lactic acid (L-lactic acid oligomers) consisting of a cyclic type with a condensation degree of 9 to 19 and a linear type with a condensation degree of 5 to 23 as a fraction eluted with 100% acetonitrile at pH 2.0. The resulting L-lactic acid oligomers were neutralized with alkali (sodium hydroxide NaOH), and then dried under a reduced pressure to obtain a raw powder. It describes that it was aseptically dissolved or suspended in an appropriate solvent to a predetermined concentration in order to prepare an injectable preparation. When used as an oral preparation, the raw powder treated in the same manner as described above can be used as it is. However, a stabilizer such as calcium lactate, calcium carbonate, mannitol, sorbitol and the like is usually added. Normally, cyclic poly L-lactic acid is a substance that is difficult to ingest because its dissolved solution shows acidity of pH 2.0 that is as high as pH 2.5 of lemon juice. Although a sweetener such as mannitol and sorbitol is used to temporarily reduce its acidity, the sourness will reappear over time. While it can be possible to raise the pH by using a sodium hydroxide (NaOH) alkali neutralizing agent, the agent will change the cyclic poly L-lactic acid to cause a problem in safety. Thus, L-lactic acid oligomer (CPL) was neutralized with 1 mol/m$^3$ sodium hydroxide (NaOH) and dried under reduced pressure. A substance containing 500 g (28%) of the sweetener sorbitol, 200 g (11%) of calcium carbonate and 800 g of the above-neutralized product has acidity remaining after the alkali neutralization treatment. The use of a large amount (39%) of the above additives will change the substance itself and further reduce its effect. As time passes, the acidity will increase, and moisture and stickiness will generate.

According to Patent Document 3, cyclic poly L-lactic acid is secreted from cells according to the state in the living body as a kind of biological defense reaction so as to improve the cell function, increases the said function in normal cells to promote a cell activation, and inhibits the metabolic process in abnormal cells to denature them. The cyclic poly L-lactic acid acts on the metabolism of intracellular organelles such as rough endoplasmic reticulum, smooth endoplasmic reticulum, ribosome, Golgi apparatus. As a result, it will suppress cell metabolism and affect protein/glycoprotein synthesis, intracellular lipid metabolism, ion transfer and transport, etc. It is also involved in ATP synthesis, synthesis of mRNA, RNA and DNA, and generation of intracellular energy. It also affects the activation of NK (natural killer) cells and anaerobic glycolysis as well.

Patent Document 3 discloses that as an action mechanism of the cyclic poly L-lactic acid, it inhibits the activity of enzymes in the anaerobic glycolysis such as pyruvate kinase and lactate dehydrogenase (LDH), which are responsible for supplying energy to cancer cells, it especially inhibits strongly the LDH activity of cancer cells. It causes morphologically vacuolation/expansion of the cytoplasm of the cancer cells, collapse/aggregation of the nuclei, and denaturation/embrittlement in the whole of the cells containing cell membranes. As a result, the growth of cancer cells is suppressed, leading to their extinction. It describes that the cyclic poly L-lactic acid is a substance that strongly inhibits the action of the intracellular organelles and affects the proliferation mechanism of the whole cells, wherein nuclear enrichment, collapse, and lysis of the cancer cells are observed almost simultaneously with cytoplasmic degeneration. It also describes that the cyclic poly L-lactic acid is obtained by dehydration polymerization of L-lactic acid by heating in the atmosphere of the inert gas such as nitrogen gas under the normal pressure or reduced pressure, and it is a mixture of linear condensate of L-lactic acid and cyclic condensate of L-lactic acid.

Patent Document 4 discloses a method for producing the cyclic poly L-lactic acid by the steps (1) to (3), comprising the polymerization step of L-lactic acid wherein the pressure is changed several times up and down while raising the temperature from 130° C. to 160° C.

PRIOR ARTS

Patent Documents

[PTL1] Patent Application Publication JP2000-239171
[PTL2] Patent Application Publication JP2001-139476
[PTL3] Patent Application Publication JP2004-155670
[PTL4] Patent JP No. 5966230

SUMMARY OF THE INVENTION

Problems to be Solved by the Invention

As the pH of the conventional substance is 2.0, the acidity will remain even after the neutralization with sodium hydroxide (NaOH) alkaline agent. A large amount of additives will be then required. The cyclic type of the substance is an oligomeric substance that is a mixture of poly L-lactic acids with a degree of polymerization of 9 to 19 and an ionic strength is 15% or less. Accordingly, it is necessary to concentrate the cyclic poly L-lactic acid itself and increase its ionic strength, and to obtain the cyclic poly L-lactic acid having a pH of 6 to 7 without blending it with the additives.

Means for Solving the Problems

As a result of various studies to solve the problems, a substance having no acidity was obtained by the following steps:

repeating dehydration condensation to increase the degree of polymerization by raising and lowering the decompression force in a particular temperature range during heating while raising and lowering the temperature so as to generate a large amount of steam. Thus, the pressure was raised and lowered several times between −(minus) 600 mmHg and −(minus) 225 mmHg in a temperature range of from 170° C. to 177° C. to generate a large amount of steam, then the decompression and nitrogen gas injection were stopped while maintaining the temperature at 193° C. Oxygen was then taken in to change the pressure to 760 mmHg and generate steam, and heat-treatment was continued for several hours. The substance was then taken out, cooled and solidified at 60° C. to give the substance without acidity. The resulting substance, cyclic poly L-lactic acid, was measured to have neutrality of pH 6.2. The analysis of the substance demonstrated that the resulting ion groups with the degree of molecular polymerization of (m/z 361) for n=5 to (m/z 721) for n=10 shown in FIG. 5 had the ionic strength of 50% or more.

Advantages of the Invention

Thus, it was confirmed that the substance obtained by the above method for the production of the cyclic poly L-lactic acid comprises the ion groups with the degree of molecular polymerization (cyclic polymerization degree) of n=5 to 10 and the ionic strength of 50% or more. The result of measuring of pH of the substance showed that it had neutrality of pH 6.2. It does not have acidity so that it will not require a neutralizing agent or sweetener, and is easy to process and to ingest.

ASPECTS OF CARRYING OUT THE INVENTION

Figure 1:
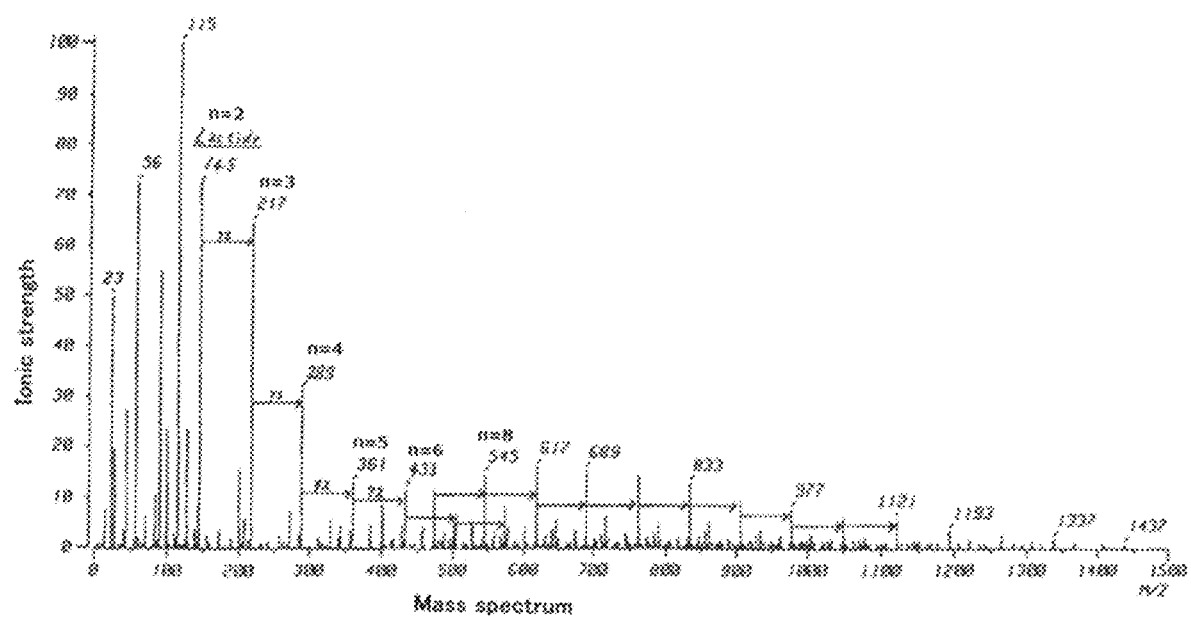
FIG. 1
The mass spectrum of Patent Document 1 is shown.

In the production method of the cyclic poly L-lactic acid, L-lactic acid solution is put into a 50 L mantle heater in a production machine tank, heat treatment is performed at a temperature of 100° C. for several hours. The pressure is then gradually reduced by a vacuum pump, and nitrogen gas is injected directly on a side area of the tank so as to stir the inside of the tank, control the pressure and discharge the generating steam. The temperature during heating is increased from 100° C. to reach the pressure of –(minus) 525 mmHg and temperature of 170° C. after 7 hours. After the pressure is further decreased to –(minus) 600 mmHg, the pressure is raised and lowered several times between –(minus) 600 mmHg and –(minus) 225 mmHg at a temperature of from 170° C. to 177° C. to generate a large amount of steam. As the temperature is raised in several hours, the pressure is decreased to the pressure of –(minus) 975 mmHg and temperature of 193° C. The decompression is then stopped while maintaining the temperature at 193° C. After the pressure is shifted to 760 mmHg, heat-treatment is continued for several hours. The substance is then taken out, and cooled and solidified at 60° C. to give a high purity substance of the cyclic poly L-lactic acid with no acidity, colorless, and transparency.

In order to examine the polymerization degree of the cyclic poly L-lactic acid, matrix-assisted laser desorption/ionization/mass spectrometry (MALDI/MS) and electrospray ionization/mass spectrometry (ESI/MS) were performed. As a result, although a monomer unit of L-lactic acid ($C_3H_4O_2$) with molecular weight distribution of m/z 72 difference was confirmed, it was also shown that the cyclic poly L-lactic acid (degree of polymerization: 5 to 30) and the chain or linear (straight) poly L-lactic acid (degree of polymerization: 2 to 30) coexisted.

[Chemical Formula 1]

The chemical formulae of the cyclic poly L-lactic acid and the chain poly L-lactic acid are shown.

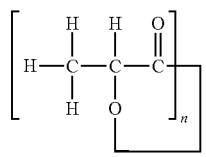

Cyclic poly L-lactic acid (degree of polymerization: 5 to 30)

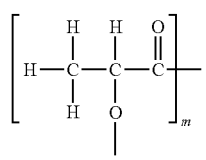

Chain poly L-lactic acid (degree of polymerization: 2 to 30)

Analytical method of the cyclic poly L-lactic acid of the present invention

Analytical apparatus

Matrix-Assisted Laser Desorption/Ionization/Mass Spectrometry (MALDI/MS)

Apparatus: rapid FLEXX TOF/TOF type manufactured by Bruker Daltonics

Measurement mode: Reflector/Positive mode

Measurement mass range: m/Z 100-4000

Electrospray Ionization/Mass Spectrometry (ESI/MS)

<Liquid Chromatograph Unit>

Apparatus: ACQUITY UPLC type manufactured by Waters

Mobile phase: 0.1% formic acid aqueous solution/acetonitrile=1/1

Flow rate: 0.2 ml/min

<Mass Analyzer>

Device: Synapt G2-S type manufactured by Waters

Measurement mode: Positive mode

Measurement mass range: m/z 50 to 2000

Analysis Method

MALDI/MS: A sample was dissolved in tetrahydrofuran, mixed with matrix (DHB) solution, and subjected to the analysis.

ESI/MS: A sample was dissolved in tetrahydrofuran and subjected to the analysis.

EXAMPLE

L-lactic acid solution (40 kg) with 90% purity was put into the 50 L mantle heater in the production machine tank, heat treatment was performed at a temperature of 100° C. for several hours. The pressure was then gradually reduced by the vacuum pump, and nitrogen gas was injected directly on the side area of the tank at 1.3 L/min so as to stir the inside of the tank, control the pressure and discharge the generating steam. The generating steam and nitrogen gas were cooled while being passed through a cooling apparatus, so that the steam was taken out as liquid and stored in a 20 L tank so as to be separated from nitrogen gas. The temperature during heating is increased from 100° C. while decompressing gradually by – (minus) 75 mmHg per 60 min to reach the pressure of – (minus) 525 mmHg and temperature of 170° C. after 7 hours. After the pressure was further decreased by – (minus) 75 mmHg per 30 min to – (minus) 600 mmHg, the pressure was raised and lowered several times between – (minus) 600 mmHg and – (minus) 225 mmHg at a temperature of from 170° C. to 177° C. to generate a large amount of steam. The pressure was further decreased by – (minus) 75 mmHg per 10 min and the temperature was according increased to reach the pressure of – (minus) 975 mmHg and temperature of 193° C. The decompression and the injection of the nitrogen gas were stopped while maintaining the temperature at 193° C. After the pressure was shifted to 760 mmHg by introducing oxygen to generate the steam, heat-treatment was continued for several hours. The substance was then taken out, cooled and solidified at 60° C. to give a high purity substance (25 kg) of the cyclic poly L-lactic acid with no acidity, colorless, and transparency.

Explanation of the Substances

| Name | Cyclic poly L-lactic acid of the present invention | Conventional cyclic poly L-lactic acid | L-lactic acid | Lactide | Poly L-lactic acid |
|---|---|---|---|---|---|
| Molecular Formula | $(C_3H_4O_2)n$ | $(C_3H_4O_2)n$ | $C_3H_6O_3$ | $C_6H_8O_4$ | $(C_3H_4O_2)n$ |
| Molecular Weight | Unit m/z 72 low molecular | Unit m/z 72 low molecular | 90.08 | 144.1 | 90,000~280,000 high molecular |
| Cyclic polymerization degree | n = 5-30 | n = 3-19  n = 9-19 | n = 1 | n = 2 | |
| Chain polymerization degree | m = 2-30 | m = 5-23 | | | |

-continued

| Name | Cyclic poly L-lactic acid of the present invention | Conventional cyclic poly L-lactic acid | L-lactic acid | Lactide | Poly L-lactic acid |
|---|---|---|---|---|---|
| Cyclic polymerization degree n = 5-10 | Ionic strength of 50% or more | Ionic strength of 15% or less | | | |
| pH | 6-7 | 2-3 | 1-2 | | |
| Acidity | no | yes | yes | | |
| Neutralizing agent | not necessary | necessary | | | |
| Sweetener | not necessary | necessary | | | |

Analysis Results and Discussion of the Cyclic Poly L-Lactic Acid of the Present Invention

MALDI/MS

Figure 2:
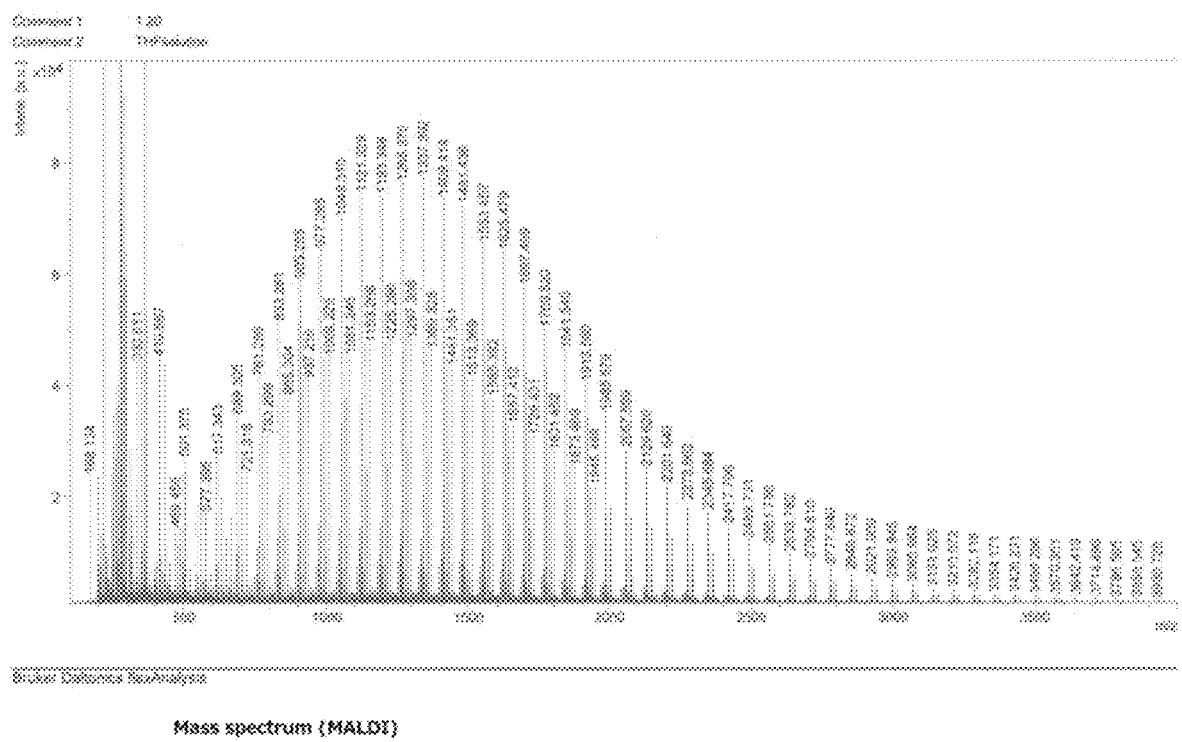
FIG. 2
The mass spectrum (MALDI) of the sample is shown.
Figure 3:
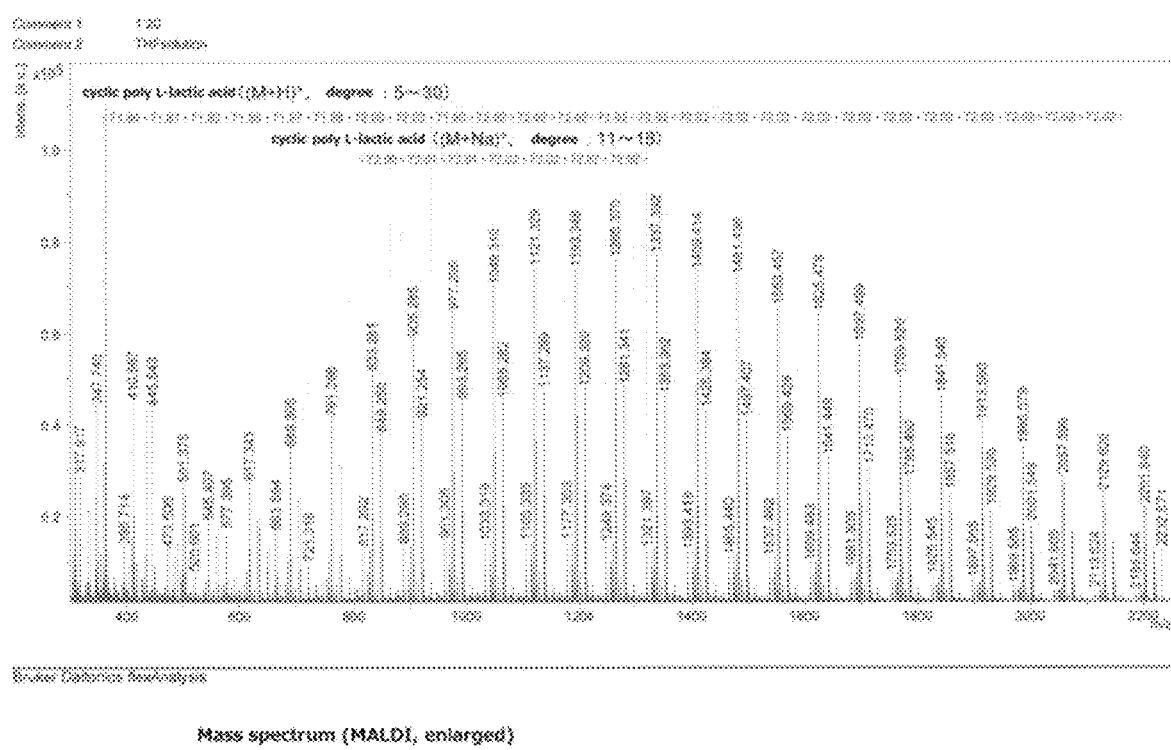
FIG. 3
The mass spectrum (MALDI, enlarged) of the sample is shown.
Figure 4:
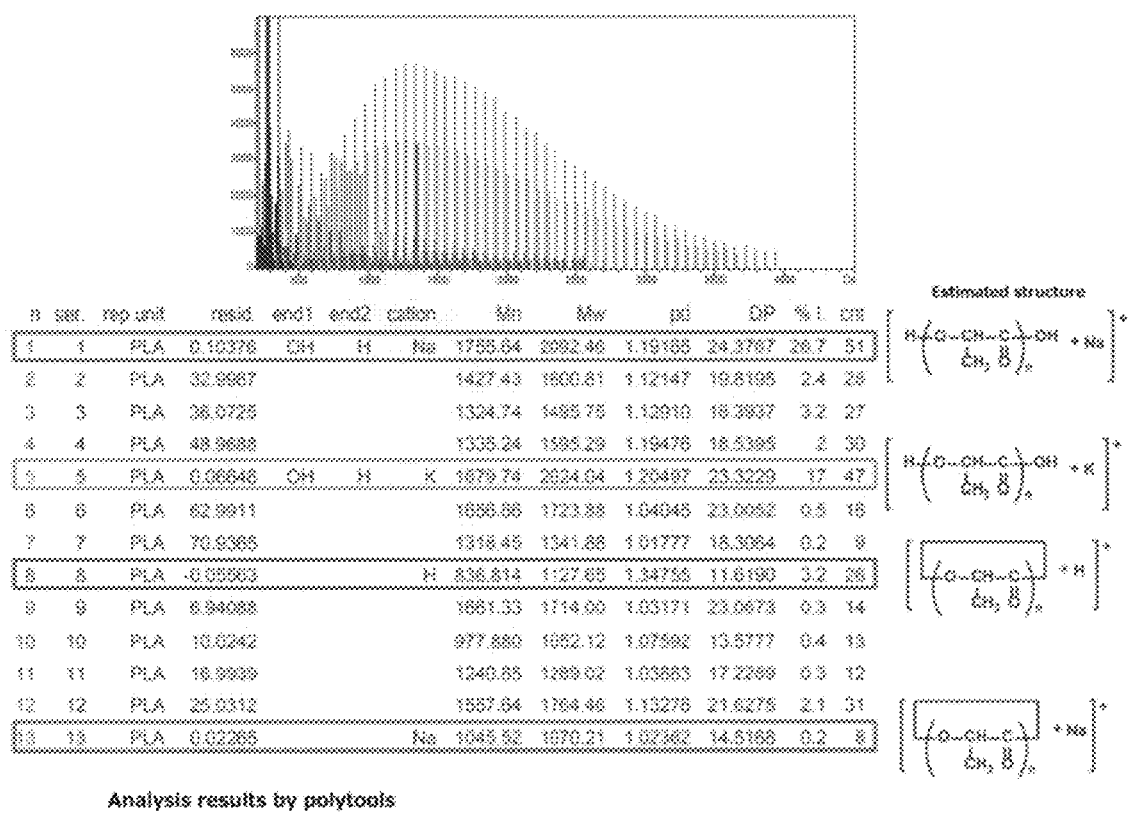
FIG. 4
The analysis result by polytools is shown.

MALDI/MS was performed to examine the degree of polymerization of the cyclic poly L-lactic acid. FIGS. 2 and 3 show the mass spectrum (MALDI) of the sample. Ion groups having a distribution of m/z 72 difference, which corresponds to a monomer unit of L-lactic acid, were confirmed. FIG. 4 shows the results of analysis by a polymer analysis software (polytools; manufactured by Bruker Daltonics). When the repeating unit is set to m/z 72 for poly lactic acid (PLA), a terminal group of the first (red) and fifth (green) ion groups (presumed as sodium ion-addition molecule $(M+Na)^+$, and potassium ion-addition molecule $(M+K)^+$, respectively) detected with a high intensity was presumed to be OH and H, respectively, suggesting that they were a chain (straight) structure. The eighth (blue) and thirteenth (blue-green) ion groups were estimated to be protonated molecules $(M+H)^+$ and $(M+Na)^+$ of the cyclic poly L-lactic acid, respectively. The ions with the thus detected degree of polymerization of 5-30 are shown in FIG. 3. The end groups of other ions were not identified.

TABLE 1

Results of Composition Estimation with the accurate mass
Elemental Composition Report
Single Mass Analysis
Tolerance = 3.0 mDa/DBE: min = −1.5, max = 50.0
Element prediction: Off
Number of isotope peaks used for i-FIT = 3
Mass Difference m/z 72

Monoisotopic Mass, Odd and Even Electron Ions
8 formula(e) evaluated with 1 results within limits (all results (up to 1000) for each mass)
Elements Used:

C: 0-100    H: 0-100    O: 0-20
161201_01 213 (0 810) Cm (208:216-114:137)

| Mass | Calc. Mass | mDa | PPM | DBE | Formula |
|---|---|---|---|---|---|
| 72.0214 | 72.0211 | 0.3 | 4.2 | 2.0 | C3 H4 O2 |

(I) Blue: 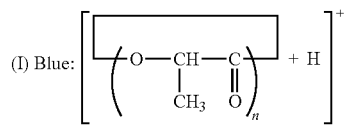

(II) Yellow: 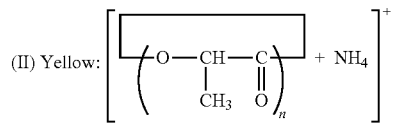

(III) Red: 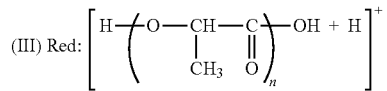

(IV) Green: 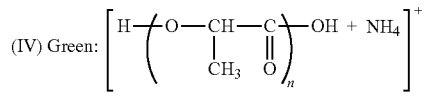

TABLE 1-continued

Monoisotopic Mass, Even Electron Ions
106 formula(e) evaluated with 2 results within limits (all results (up to 1000) for each mass)
Elements Used:

C: 0-100    H: 0-100    O: 0-20
161201_01 213 (0.810) Cm (208:216-114:137)

|  | Mass | Calc. Mass | mDa | PPM | DBE | Conf (%) | Formula |
| --- | --- | --- | --- | --- | --- | --- | --- |
| (i) Blue | 505.1567 | 505.1557 | 1.0 | 2.0 | 7.5 | 100.00 | C21 H29 O14 |
|  |  | 505.1592 | −2.5 | −4.9 | 29.5 | 0.00 | C39 H21 O |

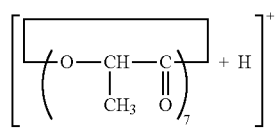

Monoisotopic Mass, Even Electron Ions
220 formula(e) evaluated with 2 results within limits (all results (up to 1000) for each mass)
Elements Used:

C: 0-100    H: 0-100    N: 0-1    O: 0-20
161201_01 213 (0.810) Cm (208:216-114:137)

|  | Mass | Calc. Mass | mDa | PPM | DBE | Conf (%) | Formula |
| --- | --- | --- | --- | --- | --- | --- | --- |
| (II) Yellow | 522.1830 | 522.1858 | −2.8 | −5.4 | 28.5 | 58.26 | C39 H24 N O |
|  |  | 522.1823 | 0.7 | 1.3 | 6.5 | 41.74 | C21 H32 N O14 |

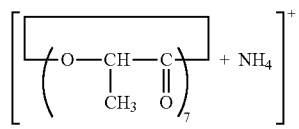

Monoisotopic Mass, Even Electron Ions
114 formula(e) evaluated with 2 results within limits (all results (up to 1000) for each mass)
Elements Used:

C: 0-100    H: 0-100    O: 0-20
161201_01 213 (0.810) Cm (208:216-114:137)

|  | Mass | Calc. Mass | mDa | PPM | DBE | Conf (%) | Formula |
| --- | --- | --- | --- | --- | --- | --- | --- |
| (III) Red | 523.1682 | 523.1663 | 1.9 | 3.6 | 6.5 | 99.99 | C21 H31 O15 |
|  |  | 523.1698 | −1.6 | −3.1 | 28.5 | 0.01 | C39 H23 O2 |

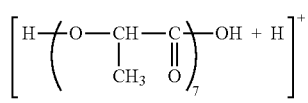

TABLE 1-continued

Monoisotopic Mass, Even Electron Ions
229 formula(e) evaluated with 2 results within limits (all results (up to 1000) for each mass)
Elements Used:

C: 0-100   H: 0-100   N: 0-1   O: 0-20
161201_01 213 (0.810) Cm (208:216-114:137)

|  | Mass | Calc. Mass | mDa | PPM | DBE | Conf (%) | Formula |
|---|---|---|---|---|---|---|---|
| (IV) Green | 540.1937 | 540.1928 | 0.9 | 1.7 | 5.5 | 100.00 | C21 H34 N O15 |
|  |  | 540.1964 | −2.7 | −5.0 | 27.5 | 0.00 | C39 H26 N O2 |

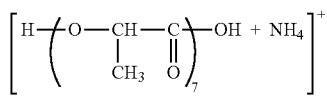

ESI/MS

Figure 5:
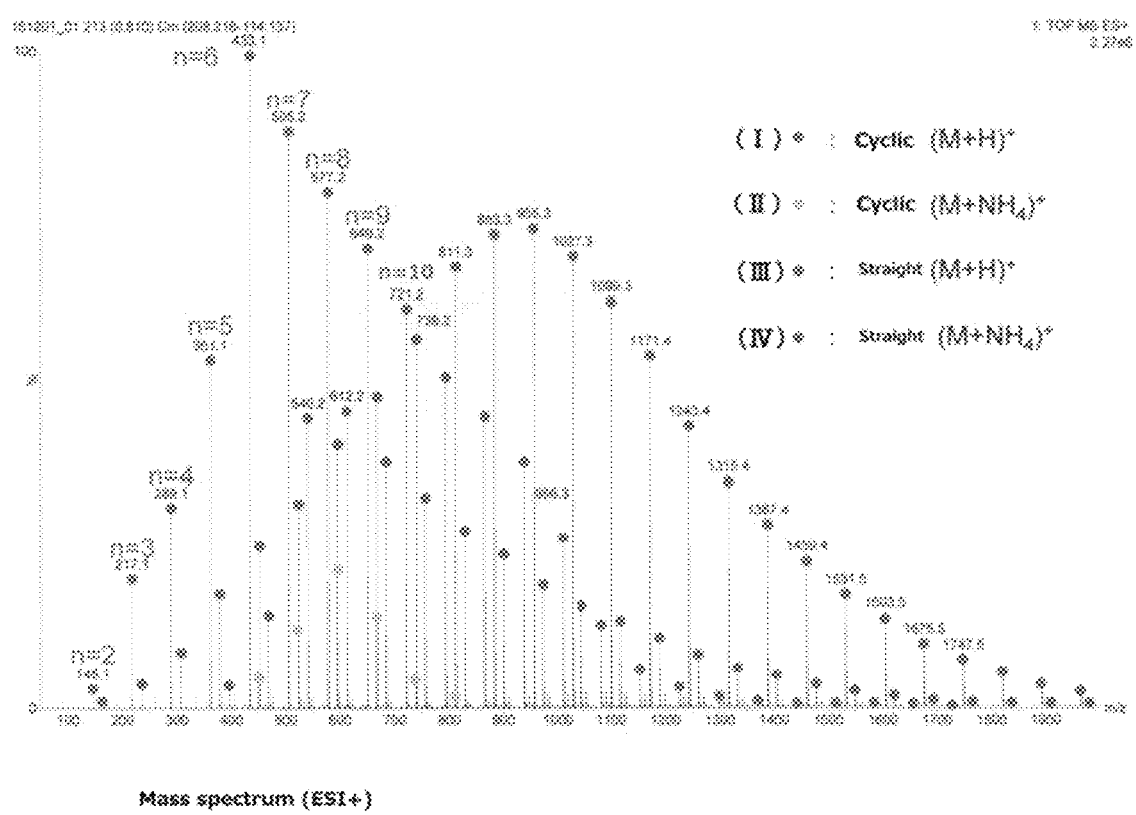
FIG. 5
The mass spectrum (ESI+) of the sample is shown.
Figure 6:
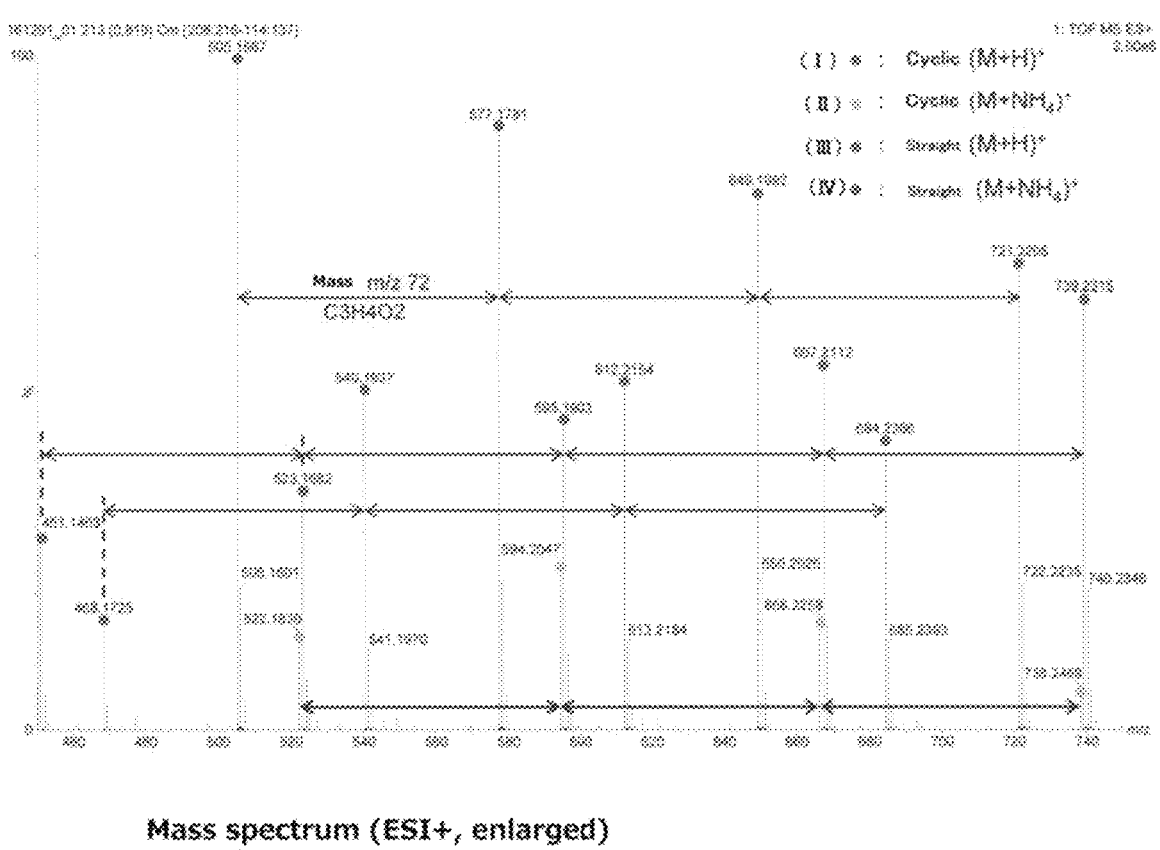
FIG. 6
The mass spectrum (ESI+, enlarged) of the sample is shown.

In order to clarify the terminal structure of the poly L-lactic acid, composition estimation was performed with ESI/MS (high resolution). The mass spectrum (ESI+) of the samples is shown in FIG. 5 and FIG. 6, and the results of composition estimation with the accurate mass are shown in Table 1. From the mass spectrum, the ion groups having a repeating unit of m/z 72 were detected, which was estimated with the accurate mass to be a lactic acid unit (C3H4O2). In addition, the composition estimation was performed for the representative ions (m/z 505, 522, 523 and 540) of the ion groups shown by (I) blue, (II) yellow, (III) red and (IV) green circles. As a result, the (I) blue and (II) yellow circles were estimated to be (M + H)$^+$ and an ammonium ion-adduct molecule (M + NH4)$^+$, respectively, of the cyclic poly L-lactic acid, and the (III) red and (IV) green circles were estimated to be (M + H)$^+$ and (M + NH4)$^+$, respectively, of the chain poly L-lactic lactic acid. In addition, ion groups having a degree of polymerization of 2 (m/z 145) or more were detected for the cyclic poly L-lactic acid.

Analytical Results of the Cyclic Poly L-Lactic Acid According to the Invention: Summary The matrix-assisted laser desorption/ionization/mass spectrometry (MALDI/MS) was performed to determine the degree of polymerization of the cyclic poly L-lactic acid. As a result, the ion groups were detected, which had the distribution of m/z 72 difference corresponding to the monomer unit of L-lactic acid. The results by the software suggested the presence of not only the cyclic poly L-lactic acid (degree of polymerization: 5 to 30) but also the chain poly L-lactic acid. Therefore, in order to investigate in more detail the terminals of the poly L-lactic acid, high resolution measurement with ESI/MS was performed. As a result, it was also presumed that the ion groups detected with ESI/MS had the cyclic (degree of polymerization: 2 or more) and chain structures.

The present invention also relates to a pharmaceutical product in which the thus newly prepared cyclic poly L-lactic acid (composition) is compounded. As described in Patent Document 3 above, it is known that the cyclic poly L-lactic acid has various physiologically actions. Therefore, based on such actions the pharmaceutical product of the present invention has various medical uses such as, for example, a metabolic regulator, a metabolic inhibitor, an immune activator (for example, activator of immune cells such as NK cells), an inhibitor of LDH activity of a cancer cell, an inhibitor/suppressor of the growth of a cancer cell, and a cancer therapeutic agent. It may be administrated orally as oral powder, tablets, capsules, and parenterally drops, injections, poultices, and the like.

An amount of Ingestion of the oral powder of the pharmaceutical product comprising the cyclic poly L-lactic acid composition of the present invention is preferably 6 to 15 g per day, and the effect can be observed in one to three months.

The effects of the pharmaceutical product according to the present invention in cases.

Case 1: Gastric Cancer and Lung Cancer Metastasis

A 70-year-old man having gastric cancer diagnosed by a medical checkup but not treated after that, and then had a medical examination again so that lung metastatic cancer was diagnosed. After daily intake of 15 g of the cyclic poly L-lactic acid powder of the present invention for 60 day, PET examination was performed to show that the lung cancer and the gastric cancer had disappeared.

Case 2: Skin Cancer

A 60-year-old woman, with brownish tumor-like breast that had been blackened daily, and shades in lungs. After daily intake of 15 g of the cyclic poly L-lactic acid powder of the present invention for 6 months, a part of the surface of the skin was removed, the shades in lungs had disappeared.

Case 3: Lung Cancer

A 62-year-old man had developed lung cancer, which was unable to treat according to the diagnosis at a hospital. After daily intake of 15 g of the cyclic polyL-lactic acid powder of the present invention for 2 months, X-ray examination revealed that the lung cancer had disappeared.

Case 4: Cervical Cancer

A 45-year-old woman with cervical cancer according to diagnosis was going to undergo surgery 3 months later. After daily intake of 6 g of the cyclic poly L-lactic acid powder daily according to the present invention for two months, an examination before the surgery revealed that the cancer had disappeared.

Case 5: Breast Cancer

A 72-year-old woman felt lumps on her chest, which was diagnosed at a hospital the next day as 20 mm breast cancer. After daily intake of 10 g of the cyclic poly L-lactic acid powder of the present invention for 1 year, MRI examination revealed that the breast cancer had disappeared.

Case 6: Colorectal Cancer

A 72-year-old man was examined to have a colorectal polyp in a specific health checkup, and 9 polyps were removed under surgery. After daily intake of 6 g of the cyclic poly L-lactic acid powder of the present invention for 1 year, one polyp was found, excised and diagnosed as a malignant tumor. No recurrence has occurred thereafter.

Case 7: Gastric Cancer

A 74-year-old man with gastric cancer according to diagnosis after an examination at a hospital. After two thirds of the stomach had been removed, he was recommended that he should immediately take surgery as the liver had also a shade, and should also take anti-cancer drug treatment. After daily intake of 10 g of the cyclic poly L-lactic acid powder of the present invention for 3 months, an endoscopic examination performed after 6 months revealed that the stomach cancer had disappeared.

Case 8: Gastric Cancer

A 64-year-old man was found to have four tumors in the stomach with a gastroscope examination under a health examination. After daily intake of 10 g of the cyclic poly L-lactic acid powder according to the present invention for 2 months, it was revealed that three tumors had disappeared and one tumor had been reduced, so that surgery could be avoided.

Case 9: Pancreatic Cancer

A 63-year-old woman was unwell and underwent a thorough examination at a hospital, so that pancreatic cancer was diagnosed.

Due to the side effect of an anti-cancer drug treatment, she had become unable to eat, and the physical fitness had accordingly declined. After daily intake of 10 g of the cyclic poly L-lactic acid powder for 2 months, MRI examination revealed that the pancreatic cancer had become smaller.

Case 10: Liver Cancer

A 65-year-old man with liver cancer diagnosed at a hospital had taken daily 10 g of the cyclic poly L-lactic acid powder of the present invention for 3 months. The results of MRI examination revealed that the liver cancer had disappeared.

Case 11: Hemangioma

A 33-year-old woman had bleeding from a tumor in two thirds of the left nose. After daily intake of 6 g of the cyclic poly L-lactic acid powder of the present invention for 2 months, the tumor had disappeared and surgery had become unnecessary according to diagnosis.

Case 12: Prostate Cancer

A 64-year-old man with hematuria had an examination in a urology department so that prostate cancer was diagnosed. A PSA value was 1519. It was said that it was difficult to treat due to decrease in physical fitness, reduction in immunity, loss of appetite, and gait difficulty. After daily intake of 10 g of the cyclic poly L-lactic acid powder of the present invention for 3 months, a re-examination showed a PSA value had gone down to 7.6.

Case 13: Colorectal Cancer

A 70-year-old man had taken the colorectal cancer surgery to remove large intestine of about 15 cm and taken medication to suppress metastasis. But, the examination of the large intestine done 2 years after the operation revealed two polyps in the intestine so that an operation was planned to be done three months later. However, after daily intake of 6 g of the cyclic poly L-lactic acid powder of the present invention for three months before the operation, an endoscopic examination revealed only one polyp remaining, which had been shrunk, and the other one had disappeared.

Case 14: Regressive Rheumatism

A 58-year-old man with continued physical abnormality and pain run throughout the body took examination at a hospital. The diagnosis result identified rheumatic rheumatism. Taking prescribed medicine had to be stopped due to the occurrence of abnormality in liver function. After daily intake of 6 g of the cyclic poly L-lactic acid of the present invention for 2 months, the pain in the whole body had been alleviated and blood test values had been also decreased.

Case 15: Cervical Cancer

A 60-year-old woman, after having undergone cervical cancer excision surgery and taken radiotherapy several times, suffered from metastasis to the vagina, which was not possible to treat. After daily intake of 10 g of the present invention cyclic poly L-lactic acid powder of the present invention for 3 months, the diagnosis by a hospital said that there had been no abnormality.

Case 16: Lung Cancer Stage 4

A 65-year-old woman having suffered from lung cancer was told after diagnosis that it was inoperable. After daily intake of 15 g of the cyclic poly L-lactic acid powder of the present invention for 3 months, MRI examination revealed that the lung cancer had become smaller.

Case 17: Small-Cell Lung Cancer

A 70-year-old man with small-cell lung cancer was admitted to a hospital, underwent surgery, and received anticancer drug treatment. Due to its metastasis to the brain, he had taken radiation therapy, and continued anti-cancer drug treatment. The anti-cancer drug treatment was then suspended. After daily intake of 10 g of the cyclic poly L-lactic acid powder of the present invention for 3 months, she had lived the same life as before as her physical condition had returned and.

Case 18: Metastasis of Uterine Cancer to the Whole Body

A 60-year-old woman was hospitalized with uterus cancer, but according to diagnosis, the cancer had metastasized to the stomach and the whole body and it could not be treated. While she had cleaned up her belongings, she had taken daily 15 g of the cyclic poly L-lactic acid powder of the present invention for 6 months. The body condition had become healthy, and it was told by the doctor that the cancer cells metastasized to the whole body had become smaller according to MRI examination by the hospital.

Case 19: Breast Cancer and Nasal Hemangioma

A 63-year-old woman had suffered from breast cancer recurrence and nasal hemangioma according to diagnosis. After daily intake of 10 g of the cyclic poly L-lactic acid powder of the present invention for 2 months, the breast cancer and the nasal hemangioma had shrunk according to the examination and diagnosis at the hospital.

Case 20: Spinal Canal Stenosis:

A 57-year-old man with sudden back pain suffered walking and unable to turn over was hospitalized. As a result of diagnosis of spinal stenosis, it was recommended that he should take surgery. After daily intake of 10 g of the cyclic poly L-lactic acid powder of the present invention for one month, the pain had suddenly disappeared and it had become possible to walk and turn over, so that surgery could be avoided.

The invention claimed is:

1. A cyclic poly L-lactic acid composition having a pH of 6 to 7 by the polymer itself,
    wherein the cyclic poly L-lactic acid has a cyclic polymerization degree (n) of 5 to 30, and
    wherein the cyclic poly L-lactic acid having the cyclic polymerization degree (n) of 5 to 10 shows an ionic strength of 50% or more.

2. The cyclic poly L-lactic acid composition according to claim 1, further comprising a chain poly L-lactic acid having a chain polymerization degree (n) of 2 to 30.

3. A pharmaceutical product in which the cyclic poly L-lactic acid composition according to claim 1 is compounded.

4. A pharmaceutical product in which the cyclic poly L-lactic acid composition according to claim 2 is compounded.

\* \* \* \* \*